United States Patent
Lacoste

(10) Patent No.: US 9,364,164 B2
(45) Date of Patent: Jun. 14, 2016

(54) NON-INVASIVE DEVICE AND METHOD FOR LOCATING A STRUCTURE SUCH AS A NERVE

(75) Inventor: Francois Lacoste, Paris (FR)

(73) Assignee: Theraclion SAS, Paris (FR)

( * ) Notice: Subject to any disclaimer, the term of this patent is extended or adjusted under 35 U.S.C. 154(b) by 594 days.

(21) Appl. No.: 12/742,065

(22) PCT Filed: Nov. 6, 2008

(86) PCT No.: PCT/FR2008/052008
§ 371 (c)(1),
(2), (4) Date: May 7, 2010

(87) PCT Pub. No.: WO2009/068793
PCT Pub. Date: Jun. 4, 2009

(65) Prior Publication Data
US 2010/0280371 A1    Nov. 4, 2010

(30) Foreign Application Priority Data

Nov. 8, 2007 (FR) .................................. 07 58884

(51) Int. Cl.
*A61B 8/00* (2006.01)
*A61B 5/0488* (2006.01)
(Continued)

(52) U.S. Cl.
CPC ............. *A61B 5/0488* (2013.01); *A61B 5/4893* (2013.01); *A61B 8/00* (2013.01);
(Continued)

(58) Field of Classification Search
CPC ........ A61B 5/0488; A61B 8/00; A61B 18/14; A61B 5/05; A61B 8/14; A61B 5/04001; A61B 5/4887
USPC .......................................... 600/407, 437, 439
See application file for complete search history.

(56) References Cited

U.S. PATENT DOCUMENTS

| 6,810,281 B2 * | 10/2004 | Brock et al. .................. 600/427 |
| 7,570,983 B2 * | 8/2009 | Becker et al. ................. 600/407 |

(Continued)

FOREIGN PATENT DOCUMENTS

| JP | 2004-520870 | 7/2004 |
| WO | 2006/129046 | 12/2006 |

OTHER PUBLICATIONS

Foley et al., "Image-Guided High-Intensity Focused Ultrasound for Conduction Block of Peripheral Nerves", Annals of Biomedical Engineering, vol. 35, No. 1, Jan. 2007, pp. 109-119.

(Continued)

*Primary Examiner* — Vani Gupta
(74) *Attorney, Agent, or Firm* — Davis & Bujold, PLLC; Michael J. Bujold

(57) ABSTRACT

Non-invasive device for locating a structure ($N_2$), such as a nerve, in a region of a body having an external surface (Se), the device comprising: a focused ultrasonic transducer (1), advantageously of the HIFU type, designed to produce an ultrasound beam (Fu) through the external surface (Se) in the region, the beam (Fu) having a focal point that can be positioned on the structure ($N_2$); monitoring means (3) for detecting a response of the structure when this is subjected to a stimulation; and stimulation means (1; 4) for stimulating the structure ($N_2$), which delivers a response detected by the monitoring means (3), the stimulation means comprising the ultrasonic transducer (1) capable of delivering an ultrasound beam (Fu) to said structure ($N_2$), so as to disturb it, characterized in that the device includes: an imager (2, 21, 22) mechanically coupled to the ultrasonic transducer (1) so that the imager follows the focal point of the transducer so as to display, on an image, the position of the focal point of the ultrasound beam (Fu) in said region of the body; and marking means, for marking the position of the structure ($N_2$) in the image produced by the imager.

8 Claims, 2 Drawing Sheets

(51) Int. Cl.
*H02K 47/04* (2006.01)
*H02K 53/00* (2006.01)
*A61B 5/05* (2006.01)
*A61B 5/04* (2006.01)
*A61B 5/00* (2006.01)
*A61B 8/14* (2006.01)

(52) U.S. Cl.
CPC .............. *H02K 47/04* (2013.01); *H02K 53/00* (2013.01); *A61B 5/04001* (2013.01); *A61B 5/05* (2013.01); *A61B 5/4887* (2013.01); *A61B 8/14* (2013.01)

(56) References Cited

U.S. PATENT DOCUMENTS 7,981,144 B2 * 7/2011 Geist et al. .................... 606/300
2003/0204135 A1 * 10/2003 Bystritsky ................ A61N 7/02 600/407
2005/0240126 A1 10/2005 Foley et al.
2006/0085049 A1 4/2006 Cory et al.
2008/0045882 A1 * 2/2008 Finsterwald ...... A61M 37/0092 604/22
2009/0149782 A1 * 6/2009 Cohen ...................... A61N 7/02 601/2
2012/0283502 A1 * 11/2012 Mishelevich ............ A61N 7/00 600/2

OTHER PUBLICATIONS

Foley et al., "Image-Guided HIFU Neurolysis of Peripheral Nerves to Treat Spasticity and Pain", Ultrasound in Med. & Biol., vol. 30, No. 9, pp. 1199-1207, 2004.

* cited by examiner

NON-INVASIVE DEVICE AND METHOD FOR LOCATING A STRUCTURE SUCH AS A NERVE

The present invention relates to the noninvasive locating of structures, such as nerves, in a zone of a body. The locating may be a step prior to treatment of the tissues neighboring the structure.

In medicine, it is often necessary to locate nerves, in particular motor nerves, in order for example to excite a muscle or else to avoid destroying the nerve during a treatment of neighboring tissues.

In general, the approximate positions of nerves are known from anatomical atlases, but it may be important to know their exact positions in a zone of the body, for example when therapeutic acts are intended to be carried out in the immediate vicinity of one, given that it is generally desirable to preserve it. The therapeutic activity may be a dissection or consist in applying energy, for example ultrasound, light (laser), radiofrequency, microwaves or radioactive energy. Knowing its position, directing the therapeutic activity onto this nerve or just beside it will be avoided in order to preserve it.

In the case for example of treating the thyroid and parathyroid glands, it is particularly important to preserve the recurrent laryngeal nerves which control the vocal cords. Another example relates to ablation of the prostate, where it is important to preserve the erector nerve.

It is also beneficial to locate sensitive nerves, for example in order to understand the origin of pain, or destroy them in order to eliminate pain.

The precise locating of nerves often poses a problem, particularly when it needs to be carried out noninvasively, outside a surgical context. Doctors use imaging (echography, MRI, X-rays, scanners) in order to locate anatomical structures, but the nerves are generally not seen by these apparatus because of the small size or an insufficient contrast. Now, numerous modern therapeutic methods are "noninvasive", that is to say nonsurgical; the activity is then guided only by the imaging.

In general, if the therapeutic act consists in a surgical intervention, the surgeon is able to see the nerves as a result of expedient and careful dissection. In case of doubt, he may also use a nerve integrity monitor such as the NIM-Response®, Nerve Integrity Monitoring System, marketed by Xomed. This apparatus comprises electrodes which the surgeon places in proximity to the nerves to be located (for example the recurrent pharyngeal nerves), and a tracheal probe which is installed in the patient's trachea during the treatments. An excitation current emitted by the electrodes travels through the tissue then the nerve; the movements of the muscles or the electrical excitation which they receive are picked up by the tracheal probe. There are other stimulators on the market, such as the Silverstein™ Facial Nerve Monitor/Stimulator, Model S8n from WR Medical Electronics Co. The movement of the vocal cords can also be detected by endoscopy.

These techniques thus make it possible to detect possible impairment of these nerves during the therapeutic activity. This is described in the application EP 1 409 079.

When the treatment is carried out at a distance from the target, however, for example by focused ultrasound (HIFU) or by means of an interstitial laser or a radiofrequency (RF) needle, direct access to the nerve is not available and there is therefore a need for a noninvasive locating method and a noninvasive locating device for precisely localizing these nerves, or more generally structures.

In order to achieve this object, the invention provides a device for noninvasively locating a structure, such as a nerve, in a zone of a body having an external surface, the device comprising a focused ultrasonic transducer advantageously of the HIFU type, adapted to produce an ultrasound beam through the external surface into the zone, the beam having a focal point which can be positioned on the structure, monitoring means for detecting a response of the structure when subjected to a stimulation, and stimulation means for stimulating the structure which delivers a response detected by the monitoring means, the stimulation means comprising the ultrasonic transducer which can deliver an ultrasound beam to said structure in order to perturb it, characterized in that the device comprises an imaging apparatus coupled mechanically to the ultrasonic transducer so that the imaging apparatus follows the focal point of the transducer in order to visualize on an image the position of the focal point of the ultrasound beam in the body zone, and marking means for marking the position of the structure on the image produced by the imaging apparatus.

Advantageously, the stimulation means comprise at least one electrode which can deliver an electrical pulse to said structure.

One principle of the invention therefore consists in insonifying the region of interest (for example that in which a nerve is looked for) by a thin beam of ultrasound, for example focused ultrasound. The ultrasound beam is scanned through the search zone and, at each position of the beam, ultrasonic pulses are emitted and the effects of this emission on the transmission of the nervous influx are observed. When the maximum effect is obtained, it is known that the nerve lies in the region of the beam with maximum intensity. The ultrasonic emitter is coupled to a medical imaging apparatus (echograph, MRI, X-ray, scanner), so that the position of the acoustic beam is known relative to the patient's anatomy. It is thus possible to locate the nerve and mark its position on the image produced by the imaging apparatus. The energy of the acoustic beam is low, so as not to destroy the nerves or the tissues in the search zone.

According to another beneficial aspect of the invention, the ultrasound may be emitted according to a sequence of pulses with variable lengths (code) in order to improve the detection threshold (reduce the necessary US power) and filter the parasitic responses of the central nervous system.

According to another beneficial aspect of the invention, the locating device furthermore comprises synchronization means for synchronizing the ultrasound beam and the stimulation so that they travel through the structure at the same time or with a determined time offset. Advantageously, the synchronization means comprise offset means adapted to generate a time offset between the ultrasound beam and the stimulation, so that the ultrasound beam arrives at the structure before the stimulation. This ensures that the ultrasound beam optimally influences the response of the structure subjected to the stimulation. When the stimulation is in the form of an electrical pulse delivered to a nerve, the duration of the pulse is very short and it is therefore preferable for the ultrasound beam to travel through the nerve slightly before the pulse crosses the nerve. This is why it is advantageous to provide a slight offset between the beam and the stimulation.

According to another advantageous aspect of the invention, the locating device comprises calculation means for determining the depth of the structure on the basis of the acoustic time of flight of the ultrasound beam in the zone and the propagation speed of the stimulation. Knowing the acoustic time of flight of the ultrasound beam and the propagation speed of the stimulation in the structure, it is readily possible to localize the axial position of the structure in depth, that is to say in the acoustic propagation direction.

According to another characteristic, the monitoring means comprise an apparatus for monitoring nerve response or an apparatus for monitoring muscle response, such as an electromyograph, an endoscope or a pressure sensor. It is thus possible to measure the response to the stimulation either directly at the structure, for example a nerve, or alternatively at an organ which depends directly on the structure, for example a muscle.

The present invention also relates to a method for noninvasively locating a structure, such as a nerve, in a zone of a body having an external surface characterized in that it comprises insonifying the structure from the external surface, monitoring the response of the structure to a stimulation and visualizing the position of the insonification of the structure. Advantageously, the method may comprise stimulation of the structure with electrical pulses or with ultrasound beams. Advantageously, the method may comprise synchronization of the insonification and the stimulation at the structure. The method may also comprise determination of the structure from the external surface on the basis of the acoustic time of flight of the ultrasound beam in the zone and the propagation speed of the stimulation.

The stimulation of the structure may thus come from an external stimulation, such as an electrical stimulation applied to a nerve with the aid of an excitation or stimulation electrode. As a variant, the stimulation may come directly from the ultrasound beam delivered by the transducer. It is then sufficient to detect directly the response to the stimulation at an organ dependent on the structure, for example a muscle. In the latter case, it is not necessary to provide specific stimulation means since the transducer will fulfill a twofold function of stimulation and locating. The device and the method of the present invention can thus be summarized as three means or steps, namely sending an ultrasound beam onto a target structure, detecting the response of the target structure and, in the event of a positive result, marking or recording the position of the target structure with the aid of an imaging apparatus coupled to the transducer.

The invention will now be described more fully with reference to the appended drawings, which give an embodiment of the invention by way of nonlimiting example.

For reasons of simplicity, reference will only be made to a nerve in the rest of the description, as an example of a target structure to be located with the aid of the noninvasive locating device and method of the present invention. Of course, types of structures other than nerves may also be located by using the present invention, whether these structures lie inside a living body or another type of body.

Figure 1:
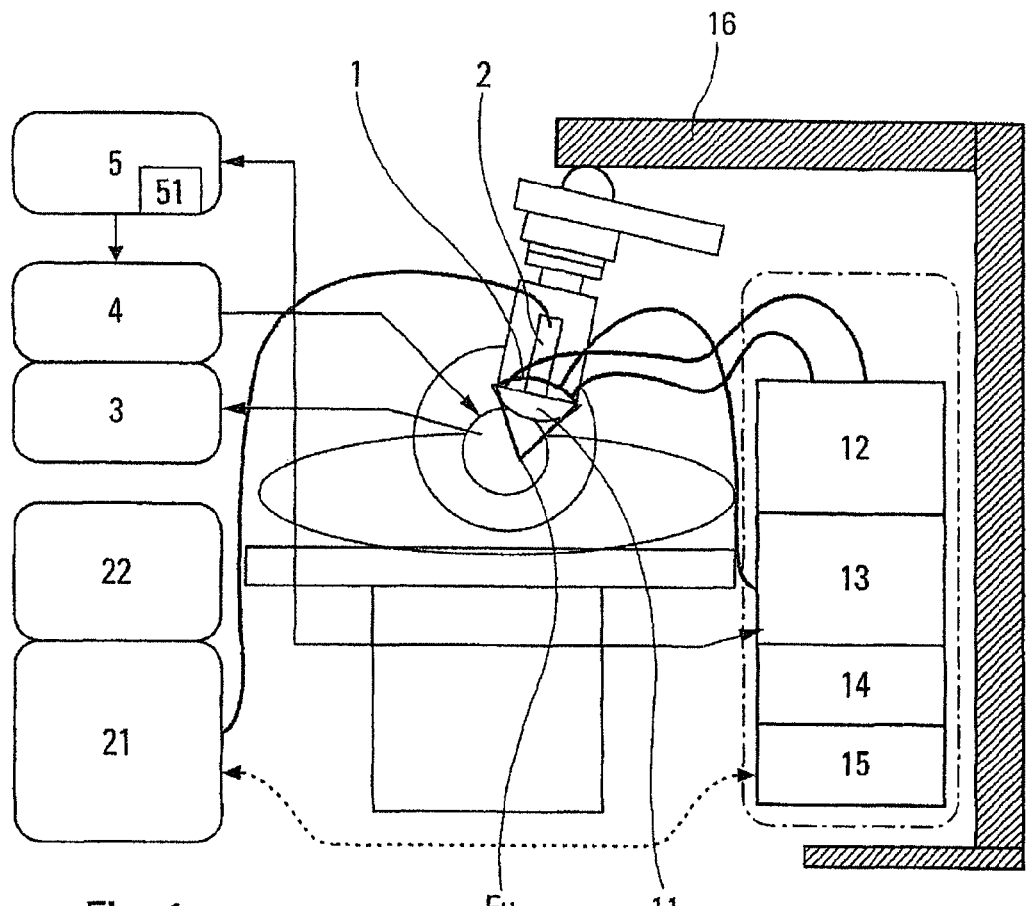
FIG. 1 is a schematic view of a locating device according to the invention.

Reference will first be made to FIG. 1 in order to describe in detail the various constituent elements of the locating device of the invention.

Figure 2:
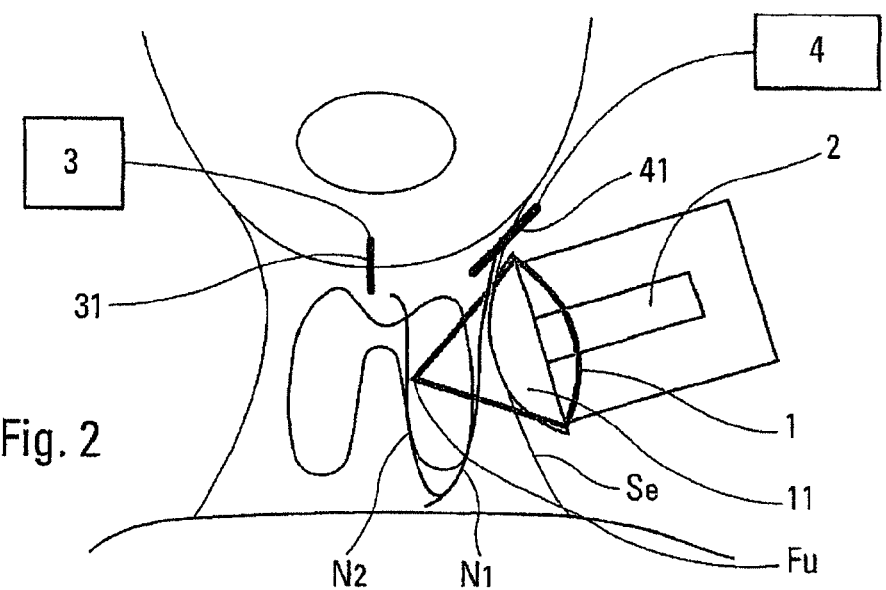
FIG. 2 is also a schematic view showing a part of the locating device of FIG. 1 in place on a patient.

The device firstly comprises an acoustic emission source 1, which may advantageously be an ultrasonic transducer adapted to produce an ultrasound beam Fu. The ultrasonic transducer is preferably of the HIFU type, making it possible to produce an ultrasound beam focused at a precise focal point. The transducer may also be of the type with linear arrays. As can be seen in FIG. 2, the transducer 1 may comprise a chamber filled with a coupling fluid, through which the ultrasound beams propagate. The chamber may, for example, be delimited by a flexible balloon intended to come in intimate contact with an external surface Se of a zone of a body where the nerve to be looked for is situated. In general, the external surface Se is the patient's skin. In order to make the coupling liquid circulate inside the chamber 11, circulation means 12 are generally provided which make it possible to regulate the flow rate and the temperature of the coupling fluid inside the chamber 11. In order to function, of course, the transducer requires a power supply 13 as well as a displacement control 14 which makes it possible to displace and localize with precision the transducer with respect to the patient. In order to do this, the transducer 1 is preferably mounted on an articulated arm 16. Lastly, the transducer is coupled to a controller 15 which makes it possible to manage all the parameters of the transducer, such as its power, its frequency, its pulse duration, etc.

The locating device of the invention also comprises imaging means, which may for example be in the form of an echographic probe 2 coupled to an echograph 21 and a display screen 22. The probe 2 is coupled mechanically to the transducer 1, as can be seen in FIGS. 1 and 2. More precisely, the probe 2 and the transducer 1 are secured to one another so that the probe 2 follows the focal point of the ultrasound beams Fu. The maximum intensity zone of the ultrasound beam Fu is always represented on the image of the screen 22. To this end, the echograph 21 may be coupled to the computer 15 of the transducer, as can be seen in FIG. 1. Instead of echographic imaging, it is possible to use MRI or X-ray imaging or a scanner.

The locating device of the invention also comprises monitoring means 3 for detecting a response of the nerve when it is subjected to a stimulation. The response of the nerve may be detected directly at the nerve in the form of an electrical response pulse, or alternatively at a muscle which the nerve controls. In the latter case, the response of the muscle may be in the form of the electrical activity of the muscle, a visually detectable activity or alternatively a pressure change or a force. Thus, apparatus of the endoscope, electromyograph or pressure gauge type, etc. may be used as monitoring means. The pressure gauge may, for example, be placed on the posterior cricoarytenoid muscle. Strictly speaking, the type of monitoring means is not a critical element for, the present invention; it is sufficient for it to be able to detect a response of the nerve subjected to a stimulation, whether this stimulation is electrical, acoustic or of another type.

The locating device of the invention also comprises a stimulation means, which may be of electrical or acoustic form. In FIG. 1, the block 4 represents electrical stimulation means comprising an excitation or stimulation electrode 41 intended to be placed so as to excite the nerve being looked for, or another nerve connected to the nerve being looked for. This is the case for example in FIG. 2 which shows a nerve $N_1$, in the case in point the vagal nerve, and a nerve $N_2$, in the case in point the recurrent laryngeal nerve. The excitation electrode, connected to the electrical stimulator 4, is placed so as to be able to excite the vagal nerve $N_1$, which will excite the recurrent laryngeal nerve $N_2$. The transducer 1, with its associated echographic probe 2, is applied against the skin of the neck so as to insonify the zone of the neck and thus send the ultrasound beams Fu onto the recurrent laryngeal nerve $N_2$. Instead of electrical stimulation, it is also possible to stimulate the nerve with the aid of an ultrasound beam. The transducer 1 can therefore be used for stimulating the nerve. The response of the nerve may be tracked by monitoring at the muscle controlled by the stimulated nerve.

Figure 3:
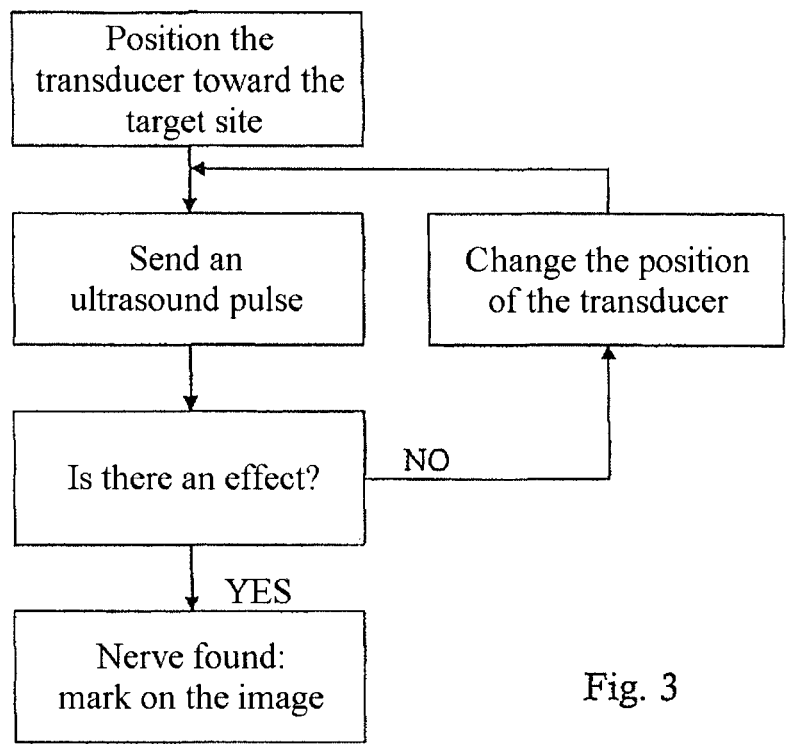
FIGS. 3 and 4 are flowcharts to explain the various steps of the locating method of the invention.

It is already known in the prior art that an applied acoustic beam perturbs, reduces, increases or cancels the electrical transmission inside nerves. This capacity of acoustic beams is employed here in order to locate the position of a nerve. The principle of the invention is based on the fact that a perturbed or induced response of the nerve is produced when the ultrasound beam is positioned on the nerve. When the nerve is stimulated with the aid of electrical pulses generated for example by a transcutaneous technique, such as the Nerve Stimulator Multi Liner from TOENIES, it is possible to monitor the response of the nerve or the response of the muscle to which the nerve is connected. The response detected by the monitoring will be perturbed by the ultrasound beam coming from the transducer, when it is positioned on the nerve. The transducer must therefore be displaced in the zone of the body where the nerve is situated, until a perturbation of the response is detected on the monitoring means. The transducer is thus displaced until this change in the response of the nerve is detected. FIG. 3 analytically schematizes the various steps of the locating method of the invention. The transducer is positioned toward the target, the ultrasonic pulse is sent, and whether there is an effect on the response of the nerve is observed. If there is no effect, the position of the transducer is changed and the operation is repeated. If there is an effect, this means that the beam is positioned on the nerve and this position should then be marked on the image visualized on the screen of the imaging apparatus.

When the stimulation is carried out with the aid of the ultrasonic transducer, the response of the nerve may be monitored at the muscle. If the muscle reacts, this again indicates that the ultrasound beam is positioned on the nerve. The reaction of the muscle may be monitored with the aid of an electromyograph, and endoscope or alternatively a pressure sensor.

It is also possible to excite the nerve via the patient's actual brain. For example, it is possible to ask the patient to perform an action and observe whether this action can still be carried out during or just after the insonification. If the intention is to locate the recurrent laryngeal nerves, for example, the patient will be asked to utter a sound, for example a monotonal sound, and either the modifications of the sound of the voice or the modifications of the characteristics of the nervous influx arriving at the muscles will be recorded by the methods described above.

The influx ultrasound beam coming from the transducer 1 must not of course be capable of destroying the nerve or the surrounding tissues in the search zone. Energy densities (calculated as the product of the ultrasound intensity times the duration of the pulses) of 1000 watts per cm$^2$×1000 milliseconds will not be exceeded. Preferably, one $10^{th}$ of this value will not be exceeded. It is also possible to use strong ultrasound powers or intensities but in a single pulse, for example similar to that used for the extracorporeal lithotripsy of renal calculus: typically, the power of the acoustic beam will lie between 100 watts per cm$^2$ and 100,000 watts per cm$^2$, and the duration of the pulse will lie between 1 microsecond and 1 millisecond, the maximum pressure being from 1 to 500 bars. The ultrasound frequencies will be a few MHz, between 0.5 and 10 MHz, and more precisely between 2 and 4 MHz. The ultrasound pulses may be single or multiple, long or short.

Figure 4:
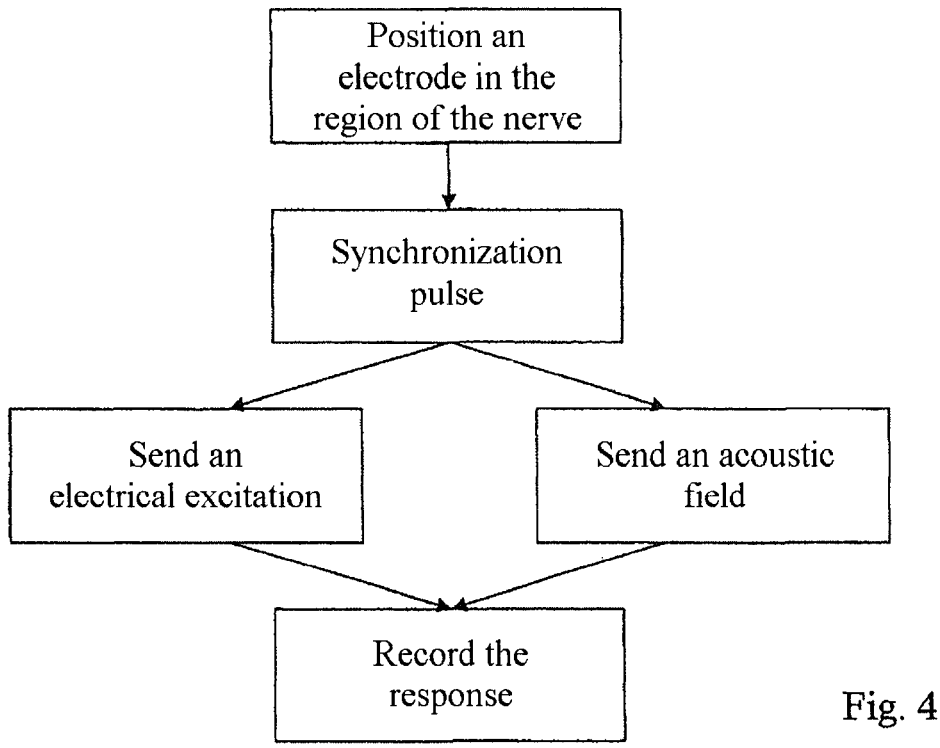

The locating device of the invention also comprises a synchronization means 5, coupled both to the transducer 1 and to the stimulation means 4, for synchronizing the ultrasound beam Fu and the electrical pulse so that they travel through the nerve at the same time. This makes it possible to optimize the effect of the ultrasound beam on the electrical response of the nerve. The synchronization may take into account the propagation time both of the nervous influx and of the ultrasound wave in the tissue, so that the pulses are synchronous overall on the insonification site, that is to say the nerve, and the detection effect is maximal. In practice, the synchronization means are connected to the power supply 13 of the transducer. According to the invention, the synchronization means also comprise offset means 51 adapted to generate an offset in time between the ultrasound beam and the electrical excitation, so that the ultrasound beam arrives at the nerve before the electrical pulse. A delay of from 5 to 20 milliseconds is optimal for reducing or increasing the transmission of the nervous flux, preferably 7 milliseconds. The ultrasound pulse will thus arrive at the nerve 7 milliseconds before the nervous pulse, so as to ensure that the nervous influx will be perturbed by the ultrasound pulse. In practice, the synchronization means deliver a synchronization pulse which triggers both the electrical excitation and the transducer. The response of the muscle may then be recorded. FIG. 4 schematically represents the various synchronization steps employed by the locating method of the invention. It starts with positioning the excitation electrode on the region of the nerve, then the synchronization pulse is emitted, the electrical excitation and the ultrasound beam are sent and the response is detected.

With the aid of the locating device and the locating method of the invention, it is also possible to determine the depth of the nerve, that is to say its position in the direction of the acoustic propagation. This is by virtue of the fact that the device comprises calculation means for determining the position of the nerve in depth on the basis of the acoustic time of flight of the ultrasound beam and the propagation speed of the nervous influx.

In all cases, the zone of interest will be excited point by point with the ultrasound beam, by displacing it between the shots or the series of shots. When the concentration zone of the beam (focal point) reaches the nerve, a response is obtained as described above. The position of the focal point, for example on the echographic image, will then be noted. The nerve to be preserved will thus have been located on the echographic images of the region to be treated.

It should be noted that the locating device and method of the invention use an ultrasonic transducer as well as an echographic probe, which may later be employed for a subsequent therapeutic treatment of the tissues neighboring the nerve. The only additional elements are then the monitoring means and the stimulation means.

The invention claimed is:

1. A device for noninvasively locating a structure, such as a nerve, in a zone of a body having an external surface, the device comprising:
    a focused ultrasonic transducer of a HIFU type, adapted to produce an ultrasound beam through the external surface into the zone, the beam having a focal point which can be positioned on the structure;
    at least one electrode which can deliver an electrical pulse to said structure for stimulating the structure; and
    a detector for detecting a response of the structure when subjected to a stimulation by said at least one electrode;
    wherein the device further comprises:
    an imaging apparatus coupled mechanically to the ultrasonic transducer so that the imaging apparatus follows the focal point of the transducer in order to visualize on an image the position of the focal point of the ultrasound beam in the zone of the body, said imaging apparatus being unable to see the structure,
    the imaging apparatus is further adapted to mark a position of the structure by marking the focal point on the image produced if the detector detects that a response of the structure to said stimulation is perturbed by the ultrasound beam, thereby determining the position of the structure, and an emitter for emitting synchronization pulses, the emitter being coupled both to the transducer and to the electrode adapted for synchronizing the ultrasound beam and the stimulation so that they travel through the structure at the same time or with a predetermined time offset, and displacement control for changing the position of the transducer if no perturbance of the response of the structure to said stimulation is detected.

2. The locating device as claimed in claim 1, wherein the emitter comprise offset means adapted to generate an offset in time between the ultrasound beam and the stimulation, so that the ultrasound beam arrives at the structure before the stimulation.

3. The locating device as claimed in claim 1, further comprising calculation means for determining the depth of the structure on the basis of the acoustic time of flight of the ultrasound beam in the zone and the propagation speed of the stimulation.

4. The locating device as claimed in claim 1, wherein the detector comprises an apparatus for monitoring nerve response or an apparatus for monitoring muscle response, such as an electromyograph, an endoscope or a pressure sensor.

5. A method for noninvasively locating a structure, such as a nerve, in a zone of a body having an external surface wherein said method comprises:
   insonifying the structure from the external surface,
   stimulating said structure with electrical pulses,
   monitoring whether the response of the structure to said stimulation is perturbed by the insonification,
   visualizing the position of the insonification of the structure by marking a position of the structure if a perturbation of the response of the structure is monitored, thereby determining the position of the structure,
   synchronizing the insonification and the stimulation of the structure, and
   changing the position of the transducer if no perturbance of the response of the structure is detected.

6. The method as claimed in claim 5, further comprising determining the depth of the structure from the external surface on the basis of the acoustic time of flight of the ultrasound beam in the zone and the propagation speed of the stimulation.

7. A device for noninvasively locating a structure, such as a nerve, in a zone of a body having an external surface, the device comprising:
   a detector for detecting a response of the structure when subjected to a stimulation,
   a focused ultrasonic transducer of a HIFU type, adapted to produce an ultrasound beam through the external surface into the zone, the beam having a focal point which can be positioned on the structure which can deliver an ultrasonic pulse to said structure for stimulating the structure which delivers a response detected by the detector;
   an imaging apparatus coupled mechanically to the ultrasonic transducer so that the imaging apparatus follows the focal point of the transducer in order to visualize on an image the position of the focal point of the ultrasound beam in the zone of the body, said apparatus being unable to see the structure;
   wherein the imaging apparatus is able to mark the position of the structure on the image produced by the imaging apparatus if the detector detects a response of the structure, to the stimulation by the HIFU and thereby determining the position of the structure, and
   displacement control for changing the position of the transducer if no response of the structure to the stimulation by the HIFU is detected.

8. A method for noninvasively locating a structure, such as a nerve, in a zone of a body having an external surface, said method comprising
   insonifying the structure from the external surface for stimulation of the structure with ultrasound beams produced by a focused ultrasonic transducer of a HIFU type,
   monitoring the response of the structure to said stimulation by the HIFU, and
   if a response of the structure to the stimulation by the HIFU is monitored, visualizing the position of the focal point of the insonification of the structure by applying a mark on an image visualized on the screen of an imaging apparatus, the imaging apparatus being unable to see the structure, thereby determining the position of the structure, and
   if there is no effect, changing the position of the transducer.

* * * * *